(12) United States Patent
Cross, Jr.

(10) Patent No.: US 7,537,245 B2
(45) Date of Patent: May 26, 2009

(54) STRAIN RELIEF DEVICE AND CONNECTOR ASSEMBLIES INCORPORATING SAME

(75) Inventor: Thomas E. Cross, Jr., St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 240 days.

(21) Appl. No.: 11/057,666

(22) Filed: Feb. 14, 2005

(65) Prior Publication Data

US 2006/0195066 A1    Aug. 31, 2006

(51) Int. Cl.
*F16L 33/00* (2006.01)
(52) U.S. Cl. .............. 285/242; 285/114; 285/131.1; 285/419; 604/533; 604/535
(58) Field of Classification Search .............. 285/242, 285/114, 115, 116, 131.1, 132.1, 419, 397, 285/398, 921; 604/264, 284, 523, 524, 533, 604/534, 535
See application file for complete search history.

(56) References Cited

U.S. PATENT DOCUMENTS

| | | | |
|---|---|---|---|
| 2,815,227 A | 12/1957 | Cullen et al. | |
| 3,447,819 A | 6/1969 | Borsum et al. | |
| 3,731,955 A | 5/1973 | Borsum et al. | |
| 4,013,310 A | 3/1977 | Dye | |
| 4,193,616 A | 3/1980 | Sarson et al. | |
| 4,310,001 A | 1/1982 | Comben | |
| 4,323,065 A | 4/1982 | Kling | |
| 4,334,551 A | 6/1982 | Pfister | |
| 4,405,163 A | 9/1983 | Voges et al. | |
| 4,473,369 A * | 9/1984 | Lueders et al. | 285/419 |
| 4,526,572 A | 7/1985 | Donnan et al. | |
| 4,581,012 A | 4/1986 | Brown et al. | |
| 4,592,749 A | 6/1986 | Ebling et al. | |
| 4,610,468 A | 9/1986 | Wood | |
| 4,632,435 A | 12/1986 | Polyak | |
| 4,636,204 A | 1/1987 | Christopherson et al. | |
| 4,650,473 A | 3/1987 | Bartholomew et al. | |
| 4,673,394 A | 6/1987 | Fenton, Jr. et al. | |
| 4,675,007 A | 6/1987 | Terry | |
| 4,691,943 A | 9/1987 | DeLand et al. | |
| 4,701,159 A | 10/1987 | Brown et al. | |
| 4,704,103 A | 11/1987 | Stöber et al. | |
| 4,723,948 A | 2/1988 | Clark et al. | |

(Continued)

FOREIGN PATENT DOCUMENTS

AU     A-21021/83      5/1985

(Continued)

OTHER PUBLICATIONS

U.S. Appl. No. 10/844,962, filed May 13, 2004, Schulte.

(Continued)

*Primary Examiner*—Aaron M Dunwoody
(74) *Attorney, Agent, or Firm*—Mueting, Raasch & Gebhardt, P.A.

(57) ABSTRACT

A connector assembly for interconnecting separate sections of tubing, e.g., catheters, and a method for using the same. Connector assemblies in accordance with embodiments of the present invention may be a two-piece construction having a connector pin and a strain relief device. The strain relief device, in addition to providing secure, substantially leak-free coupling of the tubing sections, may also provide strain relief to the tubing interconnection.

9 Claims, 8 Drawing Sheets

U.S. PATENT DOCUMENTS

| | | | |
|---|---|---|---|
| 4,772,276 A | 9/1988 | Wiita et al. | |
| 4,781,185 A | 11/1988 | Kauphusman et al. | |
| 4,786,089 A | 11/1988 | McConnell | |
| 4,823,805 A | 4/1989 | Wojcik | |
| 4,834,719 A | 5/1989 | Arenas | |
| 4,850,984 A | 7/1989 | Harris | |
| 4,880,414 A | 11/1989 | Whipple | |
| 4,890,866 A | 1/1990 | Arp | |
| 4,895,570 A | 1/1990 | Larkin | |
| 4,929,236 A | 5/1990 | Sampson | |
| 4,929,243 A | 5/1990 | Koch et al. | |
| 4,963,133 A | 10/1990 | Whipple | |
| 4,983,161 A | 1/1991 | Dadson et al. | |
| 4,994,048 A | 2/1991 | Metzger | |
| 5,000,614 A | 3/1991 | Walker et al. | |
| 5,015,013 A * | 5/1991 | Nadin | 285/64 |
| 5,040,831 A | 8/1991 | Lewis | |
| 5,053,015 A | 10/1991 | Gross | |
| 5,129,891 A | 7/1992 | Young | |
| 5,167,647 A | 12/1992 | Wijkamp et al. | |
| 5,178,612 A | 1/1993 | Fenton, Jr. | |
| 5,209,740 A | 5/1993 | Bryant et al. | |
| 5,226,898 A | 7/1993 | Gross | |
| 5,242,431 A * | 9/1993 | Kristiansen | 285/308 |
| 5,257,622 A | 11/1993 | Hooper et al. | |
| 5,279,597 A | 1/1994 | Dassa et al. | |
| 5,312,337 A | 5/1994 | Flaherty et al. | |
| 5,330,449 A | 7/1994 | Prichard et al. | |
| 5,354,282 A | 10/1994 | Bierman | |
| 5,360,418 A | 11/1994 | Weilbacher et al. | |
| 5,380,301 A | 1/1995 | Prichard et al. | |
| 5,387,192 A | 2/1995 | Glantz et al. | |
| 5,399,168 A | 3/1995 | Wadsworth, Jr. et al. | |
| 5,405,339 A * | 4/1995 | Kohnen et al. | 604/535 |
| 5,417,672 A | 5/1995 | Nita et al. | |
| 5,423,775 A | 6/1995 | Cannon | |
| 5,456,671 A | 10/1995 | Bierman | |
| 5,466,230 A | 11/1995 | Davila | |
| 5,551,849 A | 9/1996 | Christiansen | |
| 5,562,618 A | 10/1996 | Cai et al. | |
| 5,578,013 A | 11/1996 | Bierman | |
| 5,613,945 A | 3/1997 | Cai et al. | |
| 5,632,729 A | 5/1997 | Cai et al. | |
| 5,637,102 A | 6/1997 | Tolkoff et al. | |
| 5,702,371 A | 12/1997 | Bierman | |
| 5,743,873 A | 4/1998 | Cai et al. | |
| 5,827,230 A | 10/1998 | Bierman | |
| 5,830,401 A | 11/1998 | Prichard et al. | |
| 5,833,275 A | 11/1998 | Andersen | |
| 5,913,852 A | 6/1999 | Magram | |
| 5,947,931 A | 9/1999 | Bierman | |
| 5,957,968 A | 9/1999 | Belden et al. | |
| 5,971,958 A | 10/1999 | Zhang | |
| 5,993,437 A | 11/1999 | Raoz | |
| 6,068,622 A | 5/2000 | Sater et al. | |
| 6,074,379 A | 6/2000 | Prichard | |
| 6,113,572 A | 9/2000 | Gailey et al. | |
| 6,231,548 B1 | 5/2001 | Bassett | |
| 6,234,973 B1 | 5/2001 | Meador et al. | |
| 6,238,374 B1 | 5/2001 | Winkler | |
| 6,254,589 B1 | 7/2001 | Raoz | |
| 6,267,754 B1 * | 7/2001 | Peters | 604/533 |
| 6,273,404 B1 | 8/2001 | Holman et al. | |
| 6,290,676 B1 | 9/2001 | Bierman | |
| 6,332,874 B1 | 12/2001 | Eliasen et al. | |
| 6,350,260 B1 | 2/2002 | Goebel et al. | |
| 6,423,053 B1 | 7/2002 | Lee | |
| 6,428,515 B1 | 8/2002 | Bierman et al. | |
| 6,447,020 B1 | 9/2002 | Kacines et al. | |
| 6,453,185 B1 | 9/2002 | O'Keefe | |
| 6,508,807 B1 * | 1/2003 | Peters | 604/533 |
| 6,517,115 B1 | 2/2003 | Blivet | |
| 6,517,520 B2 | 2/2003 | Chang et al. | |
| 6,554,802 B1 | 4/2003 | Pearson et al. | |
| 6,562,023 B1 | 5/2003 | Marrs et al. | |
| 6,607,504 B2 | 8/2003 | Haarala et al. | |
| 6,612,624 B1 | 9/2003 | Segal et al. | |
| 6,641,177 B1 | 11/2003 | Pinciaro | |
| 6,652,489 B2 | 11/2003 | Trocki et al. | |
| 6,673,046 B2 | 1/2004 | Bierman et al. | |
| 6,676,652 B2 | 1/2004 | Mogg | |
| 6,679,528 B1 | 1/2004 | Poder | |
| 6,740,101 B2 | 5/2004 | Houser et al. | |
| 6,749,231 B2 | 6/2004 | LeMay et al. | |
| 6,749,574 B2 | 6/2004 | O'Keefe | |
| 6,796,586 B2 | 9/2004 | Werth | |
| 6,799,991 B2 | 10/2004 | Williams et al. | |
| 6,802,490 B2 | 10/2004 | Leinsing et al. | |
| 6,802,836 B2 | 10/2004 | Bouphavichith et al. | |
| 6,817,995 B1 | 11/2004 | Halpern | |
| 6,893,424 B2 | 5/2005 | Shchervinsky | |
| 6,916,051 B2 * | 7/2005 | Fisher | 285/373 |
| 2001/0049519 A1 | 12/2001 | Holman et al. | |
| 2002/0079696 A1 | 6/2002 | Szabo | |
| 2002/0082559 A1 | 6/2002 | Chang et al. | |
| 2003/0004520 A1 | 1/2003 | Haarala et al. | |
| 2003/0045912 A1 | 3/2003 | Williams et al. | |
| 2003/0077935 A1 | 4/2003 | Stein et al. | |
| 2003/0158539 A1 | 8/2003 | Bouphavichith et al. | |
| 2003/0199853 A1 | 10/2003 | Olsen et al. | |
| 2004/0039373 A1 | 2/2004 | Harding et al. | |
| 2004/0102736 A1 | 5/2004 | Bierman | |
| 2004/0111056 A1 | 6/2004 | Weststrate et al. | |
| 2004/0127854 A1 | 7/2004 | Leinsing et al. | |
| 2004/0204690 A1 | 10/2004 | Yashiro et al. | |
| 2005/0033371 A1 | 2/2005 | Sommer et al. | |
| 2005/0137614 A1 | 6/2005 | Porter et al. | |
| 2005/0143714 A1 | 6/2005 | Hegland et al. | |

FOREIGN PATENT DOCUMENTS

| | | |
|---|---|---|
| DE | 24 56 166 | 8/1976 |
| DE | 90 13 145 U1 | 1/1991 |
| EP | 0 332 943 B1 | 9/1992 |
| EP | 0 505 930 A2 | 9/1992 |
| EP | 0 474 266 A2 | 11/1992 |
| EP | 0 474 266 A3 | 11/1992 |
| EP | 0 505 930 A3 | 1/1993 |
| EP | 0 343 910 B1 | 6/1993 |
| EP | 0 360 471 B1 | 4/1994 |
| EP | 0 415 665 B1 | 1/1995 |
| EP | 0 505 930 B1 | 6/1996 |
| EP | 0 229 729 B1 | 8/1996 |
| EP | 0 552 180 B1 | 12/1996 |
| EP | 0 678 302 B1 | 2/1999 |
| EP | 0 930 083 A2 | 7/1999 |
| EP | 0 930 083 A3 | 7/1999 |
| EP | 1 138 343 A1 | 10/2001 |
| EP | 1 181 946 A1 | 2/2002 |
| EP | 1 186 316 A2 | 3/2002 |
| EP | 1 186 316 A3 | 3/2002 |
| EP | 0 691 868 B1 | 6/2002 |
| EP | 1 033 146 B1 | 7/2002 |
| EP | 1 219 319 A1 | 7/2002 |
| EP | 1 466 645 A2 | 10/2004 |
| FR | 2 586 569 | 3/1987 |
| FR | 2 612 784 | 9/1988 |
| FR | 2 750 055 | 7/1998 |
| GB | 2 343 723 A | 5/2000 |
| WO | WO 93/05844 A1 | 4/1993 |
| WO | WO 94/21319 A1 | 9/1994 |
| WO | WO 94/23775 A1 | 10/1994 |
| WO | WO 95/19801 A1 | 7/1995 |
| WO | WO 95/19802 A1 | 7/1995 |

| | | | |
|---|---|---|---|
| WO | WO 97/25562 A1 | 7/1997 |
| WO | WO 99/53981 A1 | 10/1999 |
| WO | WO 00/13743 A1 | 3/2000 |
| WO | WO 00/24462 A1 | 5/2000 |
| WO | WO 01/91825 A2 | 12/2001 |
| WO | WO 01/91825 A3 | 12/2001 |
| WO | WO 01/91847 A2 | 12/2001 |
| WO | WO 01/91847 A3 | 12/2001 |
| WO | WO 03/002171 A1 | 1/2003 |
| WO | WO 03/020368 A2 | 3/2003 |
| WO | WO 03/070151 A2 | 8/2003 |
| WO | WO 03/090840 A1 | 11/2003 |
| WO | WO 2004/016309 A2 | 2/2004 |
| WO | WO 2004/016309 A3 | 2/2004 |
| WO | WO 2004/018015 A2 | 3/2004 |
| WO | WO 2004/018015 A3 | 3/2004 |
| WO | WO 2004/052272 A2 | 6/2004 |
| WO | WO 2004/052272 A3 | 6/2004 |
| WO | WO 2004/060466 A1 | 7/2004 |
| WO | WO 2005/030316 A1 | 4/2005 |

OTHER PUBLICATIONS

U.S. Appl. No. 11/087,927, filed Mar. 23, 2005, Hegland et al.

* cited by examiner

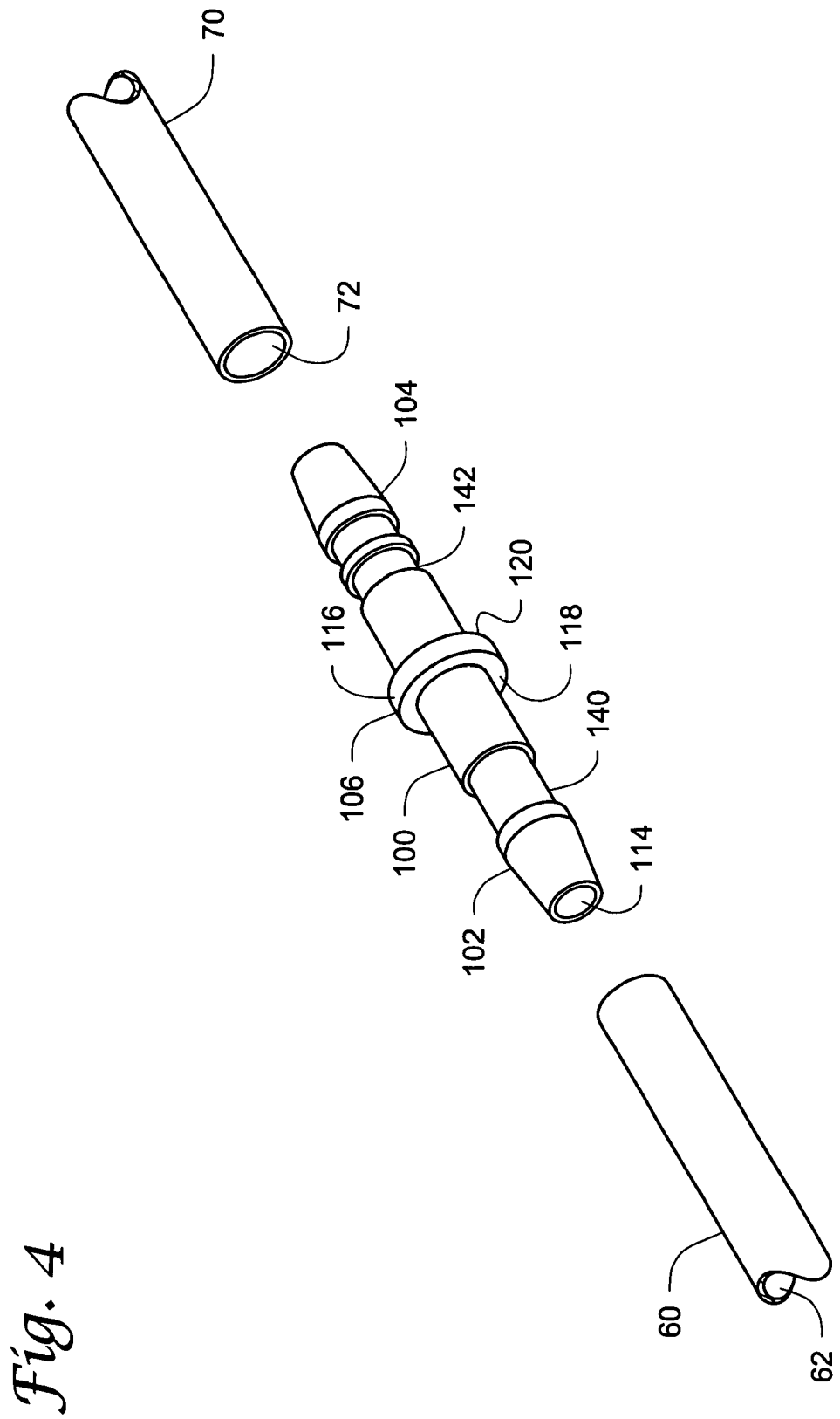

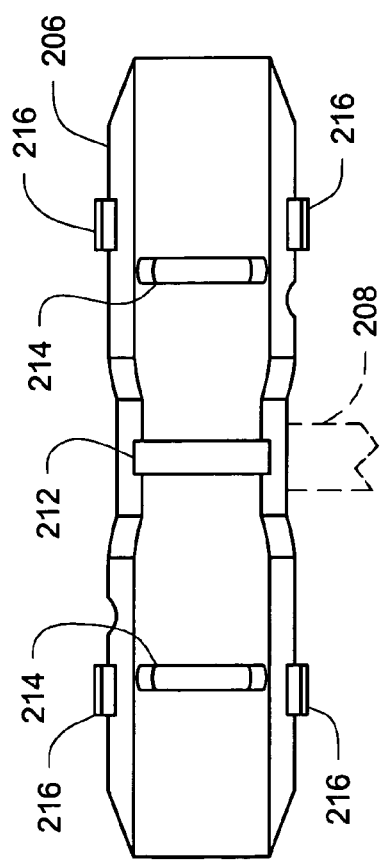
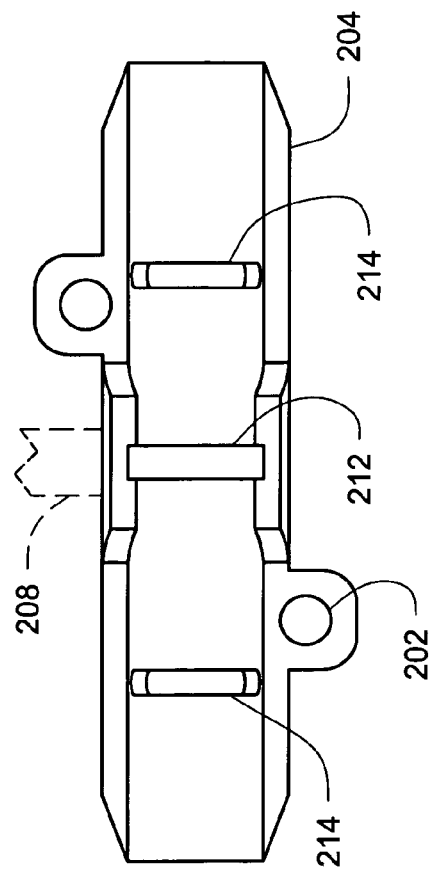
Fig. 5A
Fig. 5B ical tubing into the body involves the use of an implantable drug
STRAIN RELIEF DEVICE AND CONNECTOR ASSEMBLIES INCORPORATING SAME

TECHNICAL FIELD

The present invention relates generally to medical devices and, more particularly, to strain relief devices and connector assemblies for joining two pieces of medical tubing, and to methods for using the same.

BACKGROUND

In many medical applications, it is necessary to connect one section of medical tubing, e.g., a catheter, with another. Generally speaking, it is important that these connections be relatively secure and stable so that the tubing does not separate or develop leaks at the connection point. Security and leak-resistance take on special importance in applications where the tubing sections are implanted in a human body.

One procedure that necessitates implantation of medical tubing into the body involves the use of an implantable drug infusion pump. Such pumps are often used to control pain and/or spasticity, as well as to provide one or more drugs or fluid medications to a particular location within the body. For instance, a typical implant procedure may involve implanting a drug infusion pump into a cavity or subcutaneous pocket in the body and delivering a drug, via a catheter(s), to an epidural space or intrathecal space of the spinal column or to a particular location within the brain. In this exemplary application, a catheter assembly having two or more catheter sections, e.g., a thin-walled distal section (near the implantation site) and a thicker-walled proximal section (connected to the infusion pump), may be used to deliver the drug to the desired site.

The distal catheter section may be positioned in the desired location in the body and then connected to the proximal catheter section by use of a medical tubing connector. The connection may be made by inserting one end or prong of the connector into a lumen at one end of one catheter section (e.g., the proximal section) and the other end of the connector into a lumen of one end of the other catheter section (e.g., the distal section) and then sliding both catheter sections towards one another (toward the middle of the connector). An opposite end of the proximal section may then be connected to the drug infusion pump. Sutures may be placed around the catheter/connector prong to secure the catheter to the connector as well as to attach the catheter/connector to tissue.

While adequate for their intended purpose, inherent variability in suturing techniques may result in a suture that is incorrectly placed relative to the catheter and connector. In this case, the suture may pinch-off or otherwise interrupt normal catheter flow. Moreover, even when correctly placed, a physician may cinch the suture too tightly or, alternatively, too loosely. As a result, the suture may occlude the catheter or, if the suture is too loose, permit it to separate from the connector.

Other potential problems with some existing catheter connectors include a lack of adequate strain relief to the connection. Without proper strain relief, connector ends may damage (e.g., tear through) the catheter during or after implantation.

SUMMARY OF THE INVENTION

Embodiments of the present invention provide devices/connector assemblies and methods for connecting sections of medical tubing that may overcome these and other problems.

In one embodiment, a strain relief device for securing two catheter sections relative to a connector pin is provided. The device includes a base and an interlocking cap that, when assembled, form a tubular shell for surrounding a length of the connector pin and an overlapping portion of each of the two catheter sections. One or both of the base and cap may also include: a lock portion operable to engage the connector pin and longitudinally restrain the shell relative to the connector pin; and a compression surface located between the lock portion and each longitudinal end of the shell.

In another embodiment, a connector assembly for connecting sections of medical tubing is provided. The assembly includes a connector pin having a first end portion, a second end portion, and a lumen extending between the first end portion and the second end portion. A central portion of the pin is located between the first end portion and the second end portion, wherein the central portion has an outer dimension that is larger than an outer dimension of both the first and second end portions. The assembly also includes a strain relief device for substantially surrounding at least a longitudinal portion of the connector pin, wherein the device comprises a semi-cylindrical base and an interlocking semi-cylindrical cap. One or both of the base and cap comprises a first lock portion operable to align the device relative to the central portion.

In yet another embodiment, a method of interconnecting sections of medical tubing is provided. The method includes inserting a first end portion of a connector pin into a first medical tube. The connector pin may include an opposing, second end portion; a lumen extending between the first end portion and the second end portion; and a central portion located between the first and second end portions. The central portion may have an outer dimension that is greater than an outer dimension of either of the first and second end portions. The method also includes inserting the second end portion into a second medical tube and placing the connector pin into a base of a strain relief device. A cap of the strain relief device may then be engaged with the base such that the connector pin is substantially surrounded, along its length, by the base and cap.

In still another embodiment, a strain relief device for securing at least two catheter sections relative to a connector pin is provided. The device includes a base for covering both a first portion of the connector pin and a first portion of each of the at least two catheter sections, wherein the base has a first lock portion operable to engage the connector pin. The device also includes a cap for covering a second portion of the connector pin, wherein the cap is attachable to the base to form a tubular shell that substantially surrounds a length of the connector pin and overlapping portions of each of the at least two catheter sections.

In still another embodiment, an infusion system is provided that includes an infusion pump; an infusion catheter operatively coupled to the infusion pump; a delivery catheter implanted at a predetermined location within a body; and a connector assembly for connecting the infusion catheter to the delivery catheter. The connector assembly may include a connector pin having a first end portion; a second end portion; a lumen extending between the first end portion and the second end portion; and a central portion located between the first end portion and the second end portion. The central portion includes an outer dimension that is larger than an outer dimension of both the first and second end portions. The assembly may also include a strain relief device for substantially surrounding at least a longitudinal portion of the connector pin. The device includes a semi-cylindrical base and an interlocking semi-cylindrical cap, wherein one or both of the base and cap includes a first lock portion operable to align the device relative to the central portion.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIG. 4 is an exploded view of the connector pin and catheters of FIG. 3;

FIG. 5A is a plan view of a cap of a strain relief device in accordance with one embodiment of the present invention;

FIG. 5B is a plan view of a base of a strain relief device in accordance with one embodiment of the present invention;

DETAILED DESCRIPTION OF EXEMPLARY EMBODIMENTS

Figure 1:
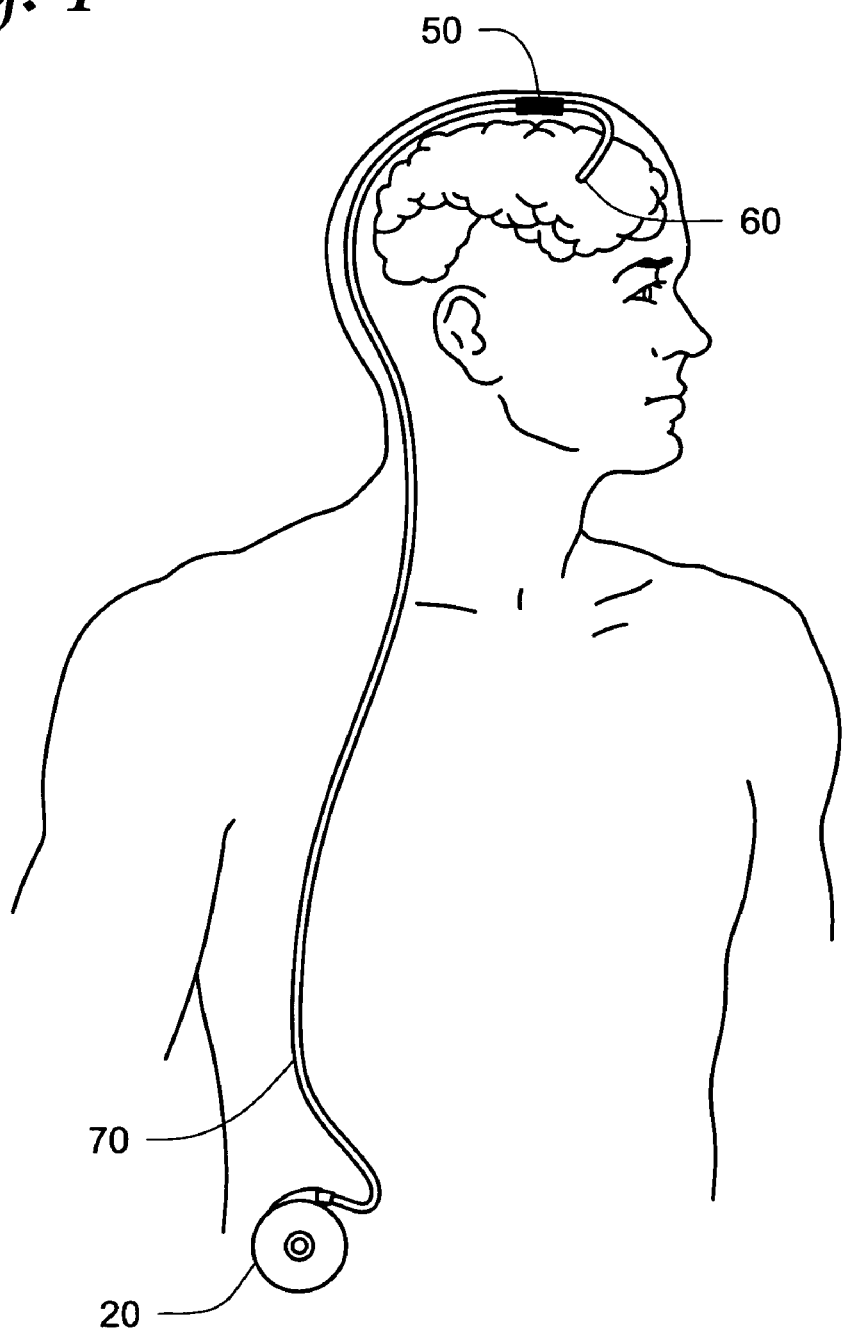
FIG. 1 is a diagrammatic view of an exemplary implanted infusion system incorporating a connector assembly in accordance with one embodiment of the invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention. Unless stated otherwise herein, the figures of the drawing are rendered primarily for clarity and thus may not be drawn to scale.

The invention is directed generally to apparatus and methods for securely coupling two pieces of tubing to one another. For example, embodiments of the present invention may be especially well-suited for joining separate sections of medical tubing, e.g., separate implantable catheters. In an embodiment of the present invention illustrated diagrammatically in FIG. 1, a connector assembly 50 for coupling a distal second catheter 70 (e.g., a drug infusion catheter that extends from a drug infusion pump 20) to a proximal first catheter 60 (e.g., a brain infusion or therapy delivery catheter) located at a pre-determined location within a human brain is provided. While the exemplary embodiments described herein are with reference to such infusion catheter couplings and methods, those of skill in the art will realize that embodiments of the present invention may find use with most any type of tubing application.

Figure 2:
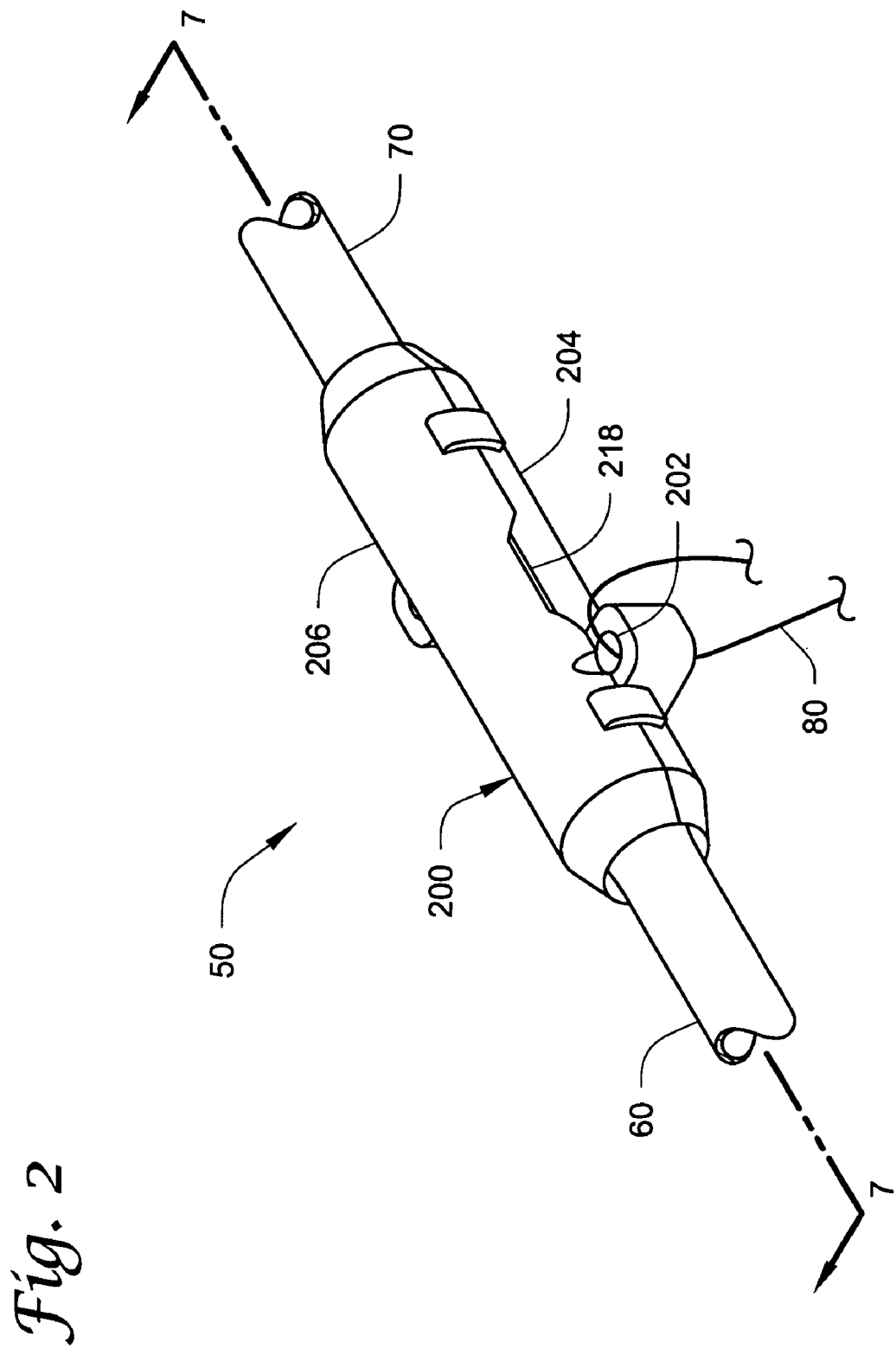
FIG. 2 is an enlarged perspective view of the exemplary connector assembly of FIG. 1, the connector assembly for use with coupling separate sections of medical tubing, e.g., catheters.
Figure 3:
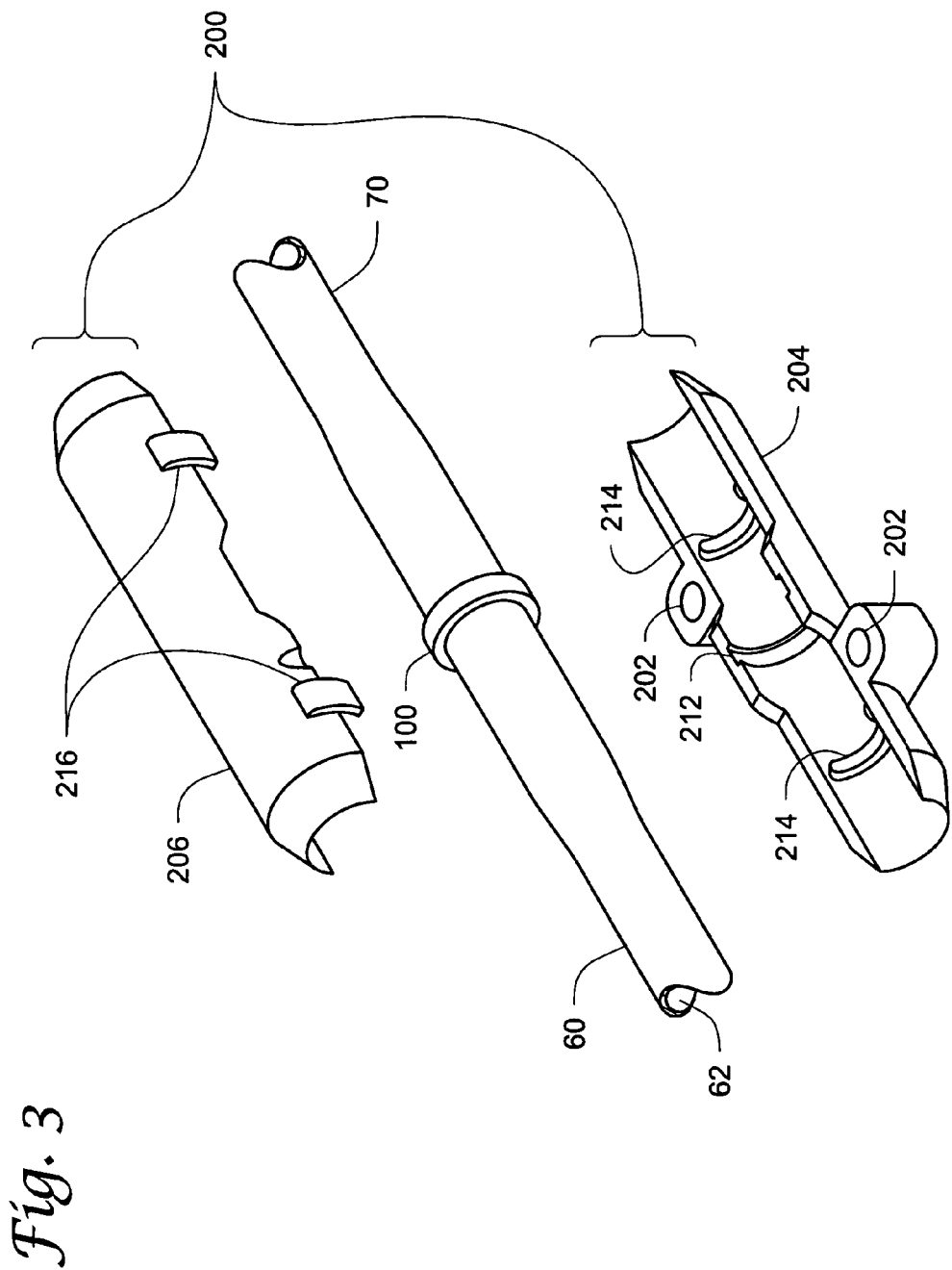
FIG. 3 is a partially exploded perspective view of the connector assembly of FIG. 2 illustrating a strain relief device and a connector pin (with catheters coupled thereto) in accordance with one embodiment of the invention.

FIGS. 2 and 3 illustrate the medical tubing connector assembly 50 in accordance with one embodiment of the invention. The assembly 50 may include a medical connector, e.g., connector pin 100 (see FIGS. 3 and 4), and a strain relief device 200. The first medical tubing section, e.g., first catheter 60, and the second medical tubing section, e.g., second catheter 70, may couple to the connector pin 100 as further described below. Once so coupled, the strain relief device 200 may surround the connector pin 100 and the catheters 60 and 70 as shown, resulting in a secure and substantially leak-free coupling.

Moreover, as further explained below, the connector assembly 50 may provide strain relief for the catheters 60 and 70. That is, the device 200 may provide resistance to tearing of the catheters 60 and 70 by the ends of connector pin 100 and further resist forces that would tend to separate, or allow relative movement of, the connector pin 100 relative to the catheters 60 and 70. The connector assembly 50 may also include securing features, e.g., one or more suture eyelets 202 on an exterior surface of the device 200, for securing the assembly relative to local tissue, e.g., with a suture 80.

FIG. 3 is a partially exploded view of the connector assembly 50, and FIG. 4 is an exploded view of the connector pin 100 and catheters 60 and 70 of FIG. 3. In these views, the connector pin 100 is illustrated as a generally longitudinal member having a first end portion 102 (see FIG. 4) operable to fit within a lumen 62 of the first catheter 60 and a second end portion 104 operable to fit within a lumen 72 of the second catheter 70. The fits between the connector pin 100 and the catheters 60 and 70 may be sufficient to hold the catheters in place, relative to the connector pin, under normal operating circumstances.

The connector pin 100 may also include a central portion 106 positioned between the first end portion 102 and the second end portion 104. The central portion 106 may have an outer or external dimension (defined by an outer surface 116 as further described below) that is larger than at least one of: an outer dimension or diameter of the first end portion 102; and an outer dimension or diameter of the second end portion 104.

The connector pin 100 may also include a lumen 114 extending through the pin from the first end portion 102 to the second end portion 104. The lumen 114, in the illustrated embodiment, may pass completely through the connector pin 100 so as to permit fluid communication between the first catheter 60 and the second catheter 70.

As used herein, the term "diameter" may refer to an effective diameter (greatest cross-sectional dimension) of any component, whether it has a circular or non-circular cross-sectional shape.

The connector pin 100 may be made of most any biocompatable material including various metals and plastics (e.g., noble materials such as titanium, and plastics such as polysulfone). Moreover, the connector pin 100 may be made as a unitary component or, alternatively, the enlarged central portion 106 may be made separately and, for example, molded to a shaft forming the first and second end portions. In the illustrated embodiments, the lumen 114 may be generally concentric to the longitudinal axis of the connector pin 100.

The end portions 102 and 104 may extend a sufficient distance from the central portion 106 to ensure adequate engagement with the catheters 60 and 70. Moreover, while the end portions 102 and 104 may be most any shape, they are preferably cylindrical (circular in cross section) to correspond with the shape of the catheter lumens into which they are inserted. The enlarged central portion 106 may be of most any shape but is also preferably cylindrical to correspond to the shape of the device 200 as further described below.

The enlarged central portion 106 may include an outer surface 116 bounded by stop surfaces 118 and 120, which are generally perpendicular to a longitudinal axis of the connector pin 100. The stop surfaces 118 and 120 may provide a positive stop against which the ends of the catheters 60 and 70, respectively, abut when the connector pin 100 is inserted therein (see FIG. 3). By providing the stop surfaces 118 and 120, the physician may ensure that each catheter 60, 70 is properly engaged with the connector pin 100. The stop surfaces 118, 120 may also assist the physician in locating the device 200 relative to the connector pin 100 as further described below.

The connector pin 100 illustrated in FIG. 4 may include end portions that include a taper. The tapers may assist in insertion of the end portions 102 and 104 into the catheters 60 and 70, respectively. The end portions 102 and 104 may also include circumferentially depressed sections 140 and 142, respectively. The circumferentially depressed sections 140 and 142 may assist in securing the catheters to the end portions 102 and 104. That is, since medical tubing is typically made of a generally compliant material, the inner surface of the tubing (e.g., catheters 60 and 70 of FIG. 3) may generally conform with the surface of the end portions of the connector pin 100, including the depressed sections 140 and 142. Other connector pin embodiments may be similar to those described in U.S. Pat. No. 5,405,339 to Kohnen et al.

The depressed sections may be configured in a variety of ways. For example, one or both of the depressed sections 140, 142 could be configured as a single depression, see e.g., depressed section 140. Alternatively, either end portion 102, 104 could have multiple depressions, see e.g., depressed section 142. The different configurations of depressed sections 140 and 142 are shown in the figures for illustration purposes as, in application, the connector pin 100 may be generally symmetrical.

The connector assembly 50 may also include the strain relief device 200, which, in the embodiment illustrated in FIGS. 2 and 3, includes a first member, e.g., a shell base 204, and an interlocking second member, e.g., a shell cap 206. The base 204 may be a generally semi-cylindrical component operable to couple with the similarly shaped cap 206. When the base 204 is attached to the cap 206 as shown in FIG. 2, the two components may form a generally tubular shell or sleeve that covers or surrounds the connector pin 100 as well as overlapping portions of catheters 60 and 70 along the longitudinal length of the connector pin 100. The device 200 may not only positively secure the catheters 60 and 70, but it may also reduce the strain on the catheters resulting from the connector pin 100. Still further, the eyelets 202, which may be provided on one or both of the base 204 and cap 206, may permit the connector assembly 50 to be anchored, e.g., sutured, to surrounding tissue.

FIGS. 5A and 5B are plan views of the base 204 and the cap 206 illustrating an interior surface of each component. While the embodiments shown and described herein include a separate base and cap, other embodiments could incorporate a joining member, e.g., a hinge 208, to couple the base 204 to the cap 206.

One or both of the base 204 and cap 206 may include a lock portion, e.g., a circumferentially-shaped groove 212 formed on an interior surface of the respective component. The groove 212 may be sized to receive the central portion 106 of the connector pin 100 (see FIG. 4) and restrain and secure the latter from longitudinal movement relative to the base 204 and cap 206.

The base 204 and cap 206 may further include one or more compression surfaces, e.g., protrusions 214, operable to hold the catheters 60 and 70 against the respective first end portion 102 (e.g., operable to push the catheter into the depressed section 140) and second end portion 104 (e.g., into the depressed section 142) of the connector pin 100 as further described below. The compression surfaces may be located on an interior surface between the lock portion (groove 212) and one or both longitudinal ends of the base 204 and cap 206.

The device 200 may further include a latch or latch members 216. In the illustrated embodiment, the latch members 216 are integrally formed on the cap 206. However, other embodiments may locate the latch members 216 on the base 204 or, alternatively, on both the base and cap 206. The latch members 216 are intended to permit positive and secure coupling of the base 204 to the cap 206 with a snap-fit. For example, each latch member 216 may form an arc-shaped lip having an inner radius that is substantially congruent to the outer shape of the base 204. As a result, the lip may deform to move past diametrical mating edges of the base 204, where it may then conform to the circular shape of the base and substantially hold the base relative to the cap 206. A small gap 218 (see FIG. 2) may be present between the assembled base and cap to permit a prying tool to be used to separate the components when desired.

As used herein, the term "snap-fit" refers to a self-locking interconnection between two or more parts wherein one or both of the parts flex sufficiently during attachment to allow the first part to move or slip past a portion of the second part until the two parts interlock with one another in a manner that generally prevents their inadvertent separation.

To provide both snap-fit coupling and the desired strain relief to the catheter ends, the base 204 and the cap 206 may be made from a relatively rigid material. Exemplary materials include polymeric materials such as polysulfone, polyurethane, and PEEK (Polyetheretherketone), and metals such as 316 Stainless Steel. In some embodiments, one or both of the base 204 and cap 206 may include an outer layer made from a material that is more pliable, e.g., softer, than a material of an underlying layer. For example, the base 204 and cap 206 could include a surface coating. Such a coating may be provided to relieve stress on surrounding tissue.

As described above, the device 200 may also include one or more eyelets 202. The eyelets 202 permit a physician to suture the device 200 to surrounding tissue during the implantation process. However, while shown and described herein as incorporating two eyelets 202 on the base 204, other embodiments may provide more, or less, eyelets. Moreover, eyelets could be located on the cap 206 as opposed to, or in addition to, the base 204.

Implantation of the connector assembly 50 of FIG. 2 will now be described with reference to FIGS. 6 and 7, the latter being a cross sectional view of the completed assembly. The connector assembly is described herein with respect to a drug or fluid medication delivery system using an implanted drug pump (not shown) operable to deliver drugs to a location within the brain or intrathecal space. As stated above, however, this application is not limiting.

A catheterization procedure may begin with the placement of a proximal catheter section (e.g., the catheter 60). The catheter 60 may be inserted in a manner known to those skilled in the art. Before, during, or after proper placement of the catheter 60 has been verified, a blunted dissected pocket may be prepared at the desired anatomical location to receive the connector assembly 50. A distal catheter section, e.g., the catheter 70, may then be tunneled between the proximal catheter 60 and a pump, e.g., infusion pump 20, which may be implanted within the torso of the patient as shown in FIG. 1. At this point in the procedure, the adjacent ends of the distal and proximal catheter sections, e.g., the coupling ends of catheters 60 and 70 that are shown in the figures, may be connected using the connector assembly 50 described herein.

Figure 6:
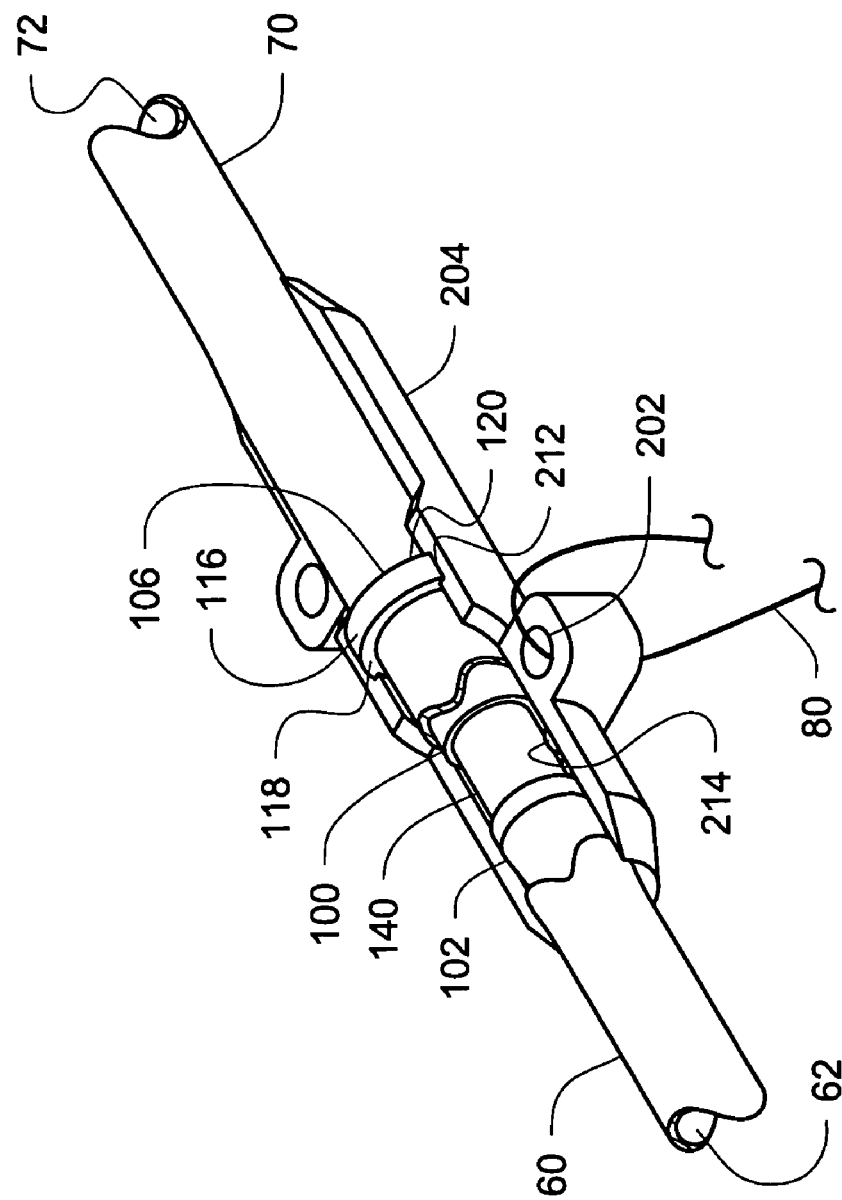
FIG. 6 illustrates an exemplary method for assembling the connector assembly of FIGS. 2 and 3.

As indicated in FIG. 6, the first end portion 102 of the connector pin 100 (in some embodiments, the connector pin may be symmetrical such that the first end portion is identical to the second end portion 104) may be inserted into the lumen 62 of the first catheter 60. The second end portion 104 may be similarly inserted into the lumen 72 of the second catheter 70. The end portions 102 and 104 of the connector pin 100 are preferably inserted into their respective catheter sections 60 and 70 until they contact the respective tubing stop surfaces 118 and 120. In practice, the implanting physician may effect the catheter connections by grasping the enlarged central portion 106 of the connector pin 100.

The outer diameter of each end portion 102 and 104 may be larger than the undeflected diameter of the lumens of the respective catheters 60 and 70 (interference fit). Alternatively, the outer diameters of the end portions 102 and 104 may be the same as, or slightly less than, the diameters of the lumens of the respective catheters (a slight clearance fit). Regardless, the resulting fit between the components, once assembled, may result in not only secure connection of the catheters 60 and 70 when the device 200 is in place, but may also provide substantially leak-free flow of fluid between the catheters. While not illustrated herein, the end portions 102 and 104 could be configured with tubing barbs, as known in the art, rather than the depressed sections described and illustrated herein.

Before, during, or after the catheters 60 and 70 are coupled to the connector pin 100, the base 204 may be secured to local tissue with the suture 80 passing through the eyelet(s) 202.

The connector pin 100, with the catheters 60 and 70 attached, may then be placed or inserted into the base 204 as shown in FIG. 6. The groove 212 ensures correct longitudinal placement of the pin 100 relative to the base 204 and/or the cap 206 during insertion. The compression surfaces, e.g., protrusions 214 (one visible in cut-away in FIG. 6), are positioned to press the catheters 60 and 70 inwardly towards the connector pin 100 at the depressed sections 140, 142.

The cap 206 may then be placed over the base 204. The cap 206 may be pushed against the base 204 until the latch members 216 of the cap engage the base with a snap-fit. The snap-fit interconnection provides positive feedback to the physician that the two components are securely assembled.

Figure 7:
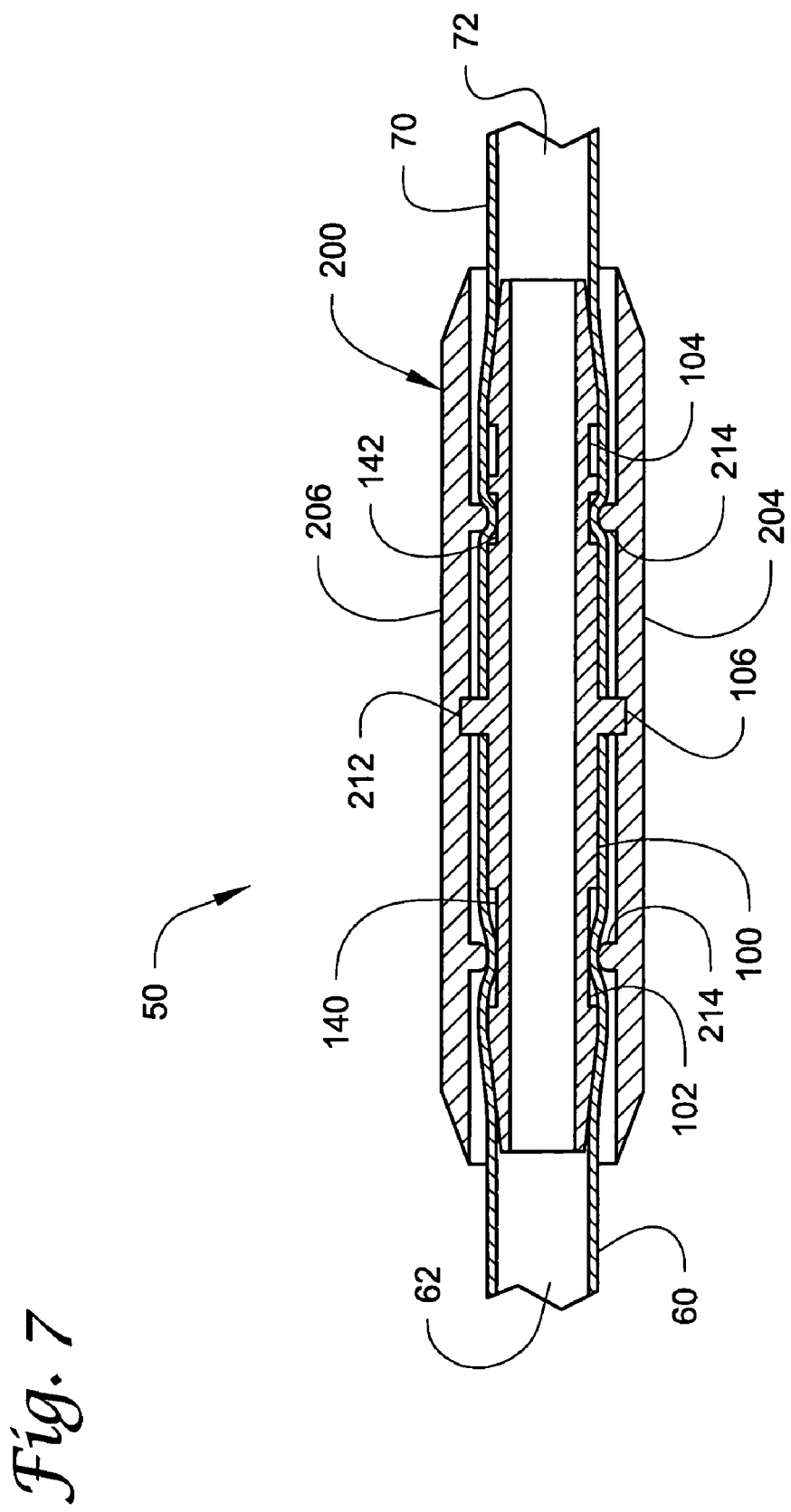
FIG. 7 is a cross section view of the connector assembly of FIG. 2 taken along line 7-7.

FIG. 7 illustrates the connector assembly 50 in cross section. As this figure illustrates, the base 204 and cap 206, when assembled, may form a tube that surrounds at least the longitudinal length of the connector pin 100 and the overlapping portions of the catheters 60 and 70. Moreover, the circumferential grooves 212 restrain the central portion 106 of the connector pin 100 and substantially reduce or eliminate relative movement between components. The protrusions 214 may press the catheters 60 and 70 inwardly in the vicinity of the depressions 140, 142. As a result, the catheters may be substantially secured relative to the connector pin 100.

The device 200 may extend to or beyond the longitudinal ends of the connector pin 100. That is, a longitudinal length of the device 200 is preferably greater than a longitudinal length of the connector pin 100. This construction may reduce the chance of the connector pin 100 puncturing the catheters 60, 70.

The size of medical tubing connector assembly 50 may vary depending upon the size of the tubing to be connected. In one exemplary embodiment, the catheters 60 and 70 may have an undeflected lumen diameter of about 0.02 to about 0.03 inches (in), e.g., about 0.024 in (0.61 millimeters (mm)). Similarly, the undeflected outer diameter of the first catheter 60 and the second catheter 70 may be about 0.042 in (1.06 mm) and 0.089 in (2.26 mm), respectively (not shown to scale).

In some embodiments, the connector pin 100 may have a length of about 0.4 to about 0.5, e.g., about 0.46 in (11.7 mm), while the untapered outer diameter of each end portion 102 and 104 may be about 0.056 in (1.4 mm). The depressed sections 140, 142 may extend inwardly about 0.006 in (0.15 mm), while the outer diameter of the enlarged central portion 106 may be about 0.08 to about 0.09 in, e.g., about 0.086 in (2.18 mm).

The device 200 may, in some embodiments, have a length of about 0.4 to about 0.6 in, e.g., about 0.5 in (13 mm), an outer diameter of about 0.09 to about 0.12 in, e.g., about 0.106 in (2.6 mm), and an inner diameter of about 0.07 to about 0.09 in, e.g., about 0.08 in (2 mm). The protrusions 214 may extend inwardly from the inner diameter of the cap and base about 0.008 to about 0.012 in, e.g., about 0.010 in (0.25 mm). As those of skill in the art will appreciate, the dimensions provided above for the catheters 60 and 70, the pin 100, and the device 200 are exemplary only. Other embodiments may utilize other relative dimensions without departing from the scope of the invention.

Figure 8:
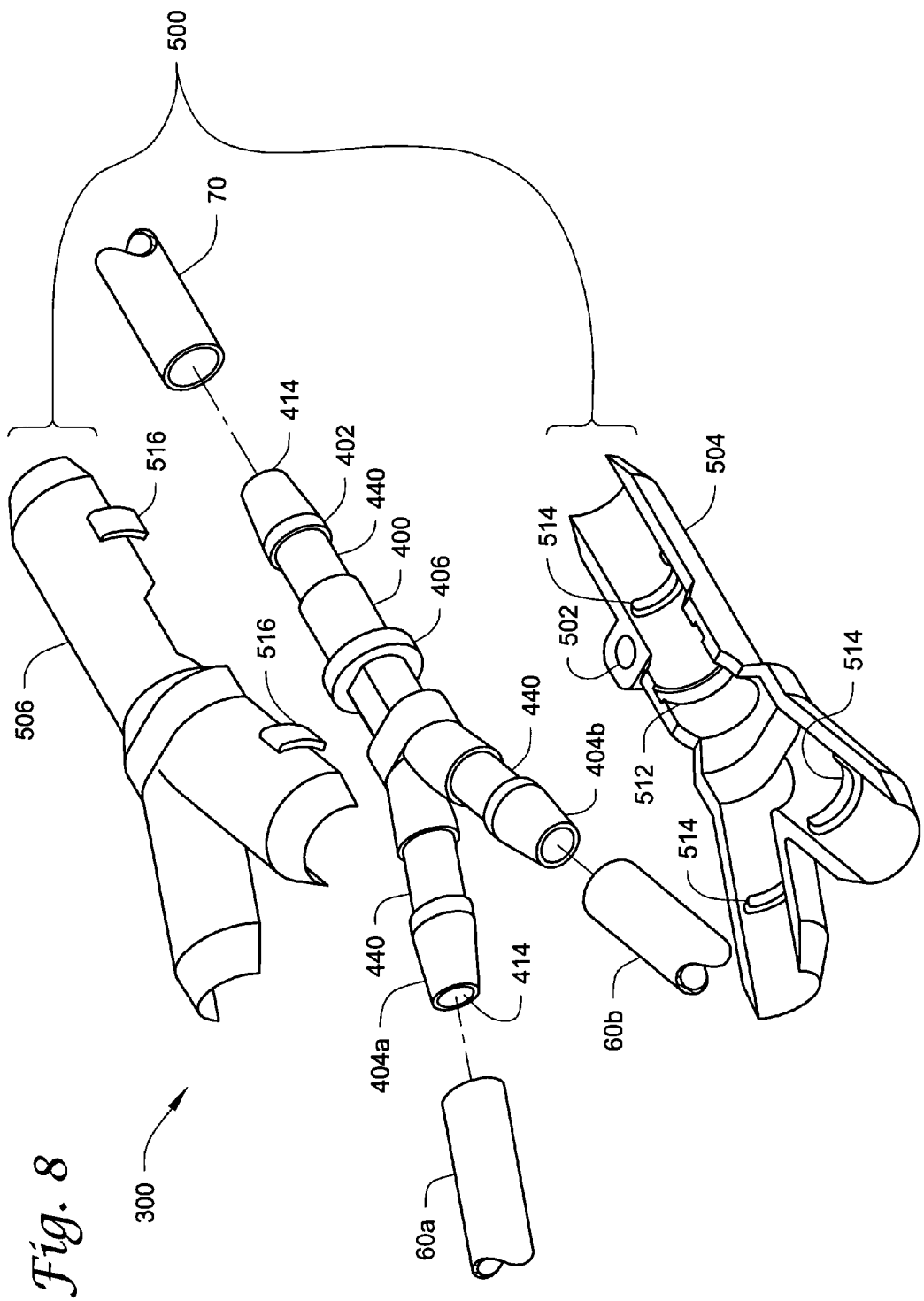
FIG. 8 is an enlarged perspective view of a connector assembly in accordance with another embodiment of the invention.

FIG. 8 illustrates a tubing connector assembly 300 in accordance with another embodiment of the present invention. The assembly 300 may function in much the same way as the assembly 50 described above. However, as FIG. 8 illustrates, the connector assembly 300 may be utilized in a branched, e.g., Y-shaped, catheter system.

The assembly 300 may include a Y-shaped connector pin 400 similar in most respects to the connector pin 100 already described above. The connector pin 400 may have a first end portion 402 operable to couple to the infusion catheter, e.g., second catheter 70 (see also FIG. 2). The flow through the catheter 70 may be divided by the connector pin 400 such that it is then provided to two or more delivery catheters, e.g., first catheters 60a and 60b, coupled to second end portions 404a and 404b of the connector pin 400. The first and second end portions may be configured generally as described above with respect to the connector pin 100. For example, each end portion 402, 404a, and 404b may include a taper and one or more depressed sections 440. The connector pin 400 may further include a central portion 406 and a lumen 414 interconnecting the first end portion 402 to the two or more second end portions 404a, 404b.

The assembly 300 may further include a strain relief shell 500. The shell 500, like the shell 200 described above, may include one or more suture eyelets 502, a base 504, and a cap 506. The base and cap 504, 506 are configured to couple to one another, e.g., via latch members 516, and surround the connector pin 400 and an overlapping portion of each catheter 70 and 60a, 60b. With the exception of the structure provided to accommodate the branching ends 404a, 404b, the shell 500 may be substantially similar to the shell 200 described above. For example, the base 504 and cap 506 may each include a lock portion 512 (only visible on base 504) operable to receive the central portion 406 and longitudinally restrain the shell 500 relative to the connector pin 400. Similarly, the base 504 and cap 506 may each include one or more compression surfaces, e.g., protrusions 514, operable to push the catheters 70 and 60a, 60b inwardly towards the connector pin near the respective end portions 402 and 404a, 404b as already described above. Implantation and assembly of the assembly 300 is therefore substantially similar to that of the assembly 50 already described herein.

While the embodiments described and illustrated herein are directed to connector assemblies that provide branching from one input to either one or two outlets, such configurations are not limiting. In fact, those of skill in the art will appreciate that the present invention may find application to connector assemblies having almost any number of input and output connections.

Connector assemblies in accordance with embodiments of the present invention may provide a secure method and apparatus for connecting separate sections of medical tubing by using a connector pin and strain relief device. Moreover, connector assemblies in accordance with embodiments of the present invention provide not only secure coupling, but also strain relief to the catheter connection. Moreover, by separating the anchoring suture(s) from the catheter retaining function, variability in suturing technique may not directly impact the catheter, e.g., a tight (or loose) suture will not result in occlusion (or separation) of the catheter.

The complete disclosure of the patents, patent documents, and publications cited in the Background, the Detailed Description of Exemplary Embodiments, and elsewhere herein are incorporated by reference in their entirety as if each were individually incorporated.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

What is claimed is:

1. A connector assembly for connecting first and second sections of medical tubing, the assembly comprising:
   a connector pin comprising:
      a first end portion receivable within the first section of medical tubing and a second end portion receivable within the second section of medical tubing, wherein the first end portion and the second end portion each define a circumferentially depressed section; and
      a central portion located between the first end portion and the second end portion, wherein the central portion has an outer diameter that is larger than an outer diameter of both the first and second end portions; and
   a strain relief device for substantially surrounding at least a longitudinal portion of the connector pin and overlapping portions of the first and second sections of medical tubing, wherein the device comprises a semi-cylindrical base and an interlocking semi-cylindrical cap, wherein the base and cap each comprise:
      a lock portion operable to align the device relative to the central portion;
      a first interior surface of uniform diameter extending from the lock portion to a first end of the device, and a second interior surface of uniform diameter extending from the lock portion to a second end of the device; and
      an inwardly extending protrusion formed on each of the first interior surface and the second interior surface such that each of the protrusions of the base and cap is positioned to align with one of the circumferentially depressed sections of the first and second end portions of the connector pin when the connector pin is surrounded by the strain relief device.

2. The assembly of claim 1, wherein each inwardly extending protrusion comprises a compression surface.

3. The assembly of claim 1, wherein the device has a longitudinal length greater than a longitudinal length of the connector pin.

4. The assembly of claim 1, wherein the base and the cap comprise a polymeric material.

5. The assembly of claim 4, wherein the polymeric material comprises polysulfone.

6. The assembly of claim 1, wherein the connector pin branches from the first end portion to two or more second end portions.

7. The assembly of claim 1, wherein the first end portion is operable to couple to an infusion catheter, and the second end portion is operable to couple to a therapy delivery catheter implanted at a predetermined location within a body.

8. The assembly of claim 7, wherein the infusion catheter is attached to an implantable infusion pump.

9. The assembly of claim 1, wherein the inwardly extending protrusions extend normal to a longitudinal axis of the strain relief device.

* * * * *